United States Patent
Mansouri et al.

(10) Patent No.: US 10,857,077 B2
(45) Date of Patent: *Dec. 8, 2020

(54) SUNSCREEN COMPOSITIONS COMPRISING UNIFORM, RIGID, SPHERICAL, NANOPOROUS CALCIUM PHOSPHATE PARTICLES AND METHODS OF MAKING AND USING THE SAME

(71) Applicant: Laboratory Skin Care, Inc., Redwood City, CA (US)

(72) Inventors: Zahra Mansouri, Redwood City, CA (US); Rodica-Tatiana Canelide, Redwood City, CA (US); Douglas Thomas, Palo Alto, CA (US); Tetsuro Ogawa, Tokyo (JP)

(73) Assignee: Laboratory Skin Care, Inc., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/156,190

(22) Filed: Oct. 10, 2018

(65) Prior Publication Data

US 2020/0060949 A1 Feb. 27, 2020

Related U.S. Application Data

(63) Continuation of application No. 15/490,630, filed on Apr. 18, 2017, now Pat. No. 10,123,950, which is a continuation of application No. 14/752,599, filed on Jun. 26, 2015, now Pat. No. 9,642,784, which is a continuation of application No. 12/943,887, filed on Nov. 10, 2010, now Pat. No. 9,095,510.

(60) Provisional application No. 61/259,935, filed on Nov. 10, 2009.

(51) Int. Cl.
| | |
|---|---|
| *A61Q 17/04* | (2006.01) |
| *A61K 8/02* | (2006.01) |
| *A61K 8/24* | (2006.01) |
| *A61K 8/27* | (2006.01) |
| *A61K 8/29* | (2006.01) |
| *A61K 8/37* | (2006.01) |
| *A61K 8/40* | (2006.01) |

(52) U.S. Cl.
CPC ............ *A61K 8/025* (2013.01); *A61K 8/0279* (2013.01); *A61K 8/24* (2013.01); *A61K 8/27* (2013.01); *A61K 8/29* (2013.01); *A61K 8/37* (2013.01); *A61K 8/40* (2013.01); *A61Q 17/04* (2013.01); *A61K 2800/412* (2013.01); *A61K 2800/56* (2013.01); *A61K 2800/5922* (2013.01); *A61K 2800/60* (2013.01)

(58) Field of Classification Search
CPC . A61K 8/24; A61K 8/025; A61K 8/37; A61K 8/40; A61K 8/0279; A61K 2800/60; A61K 2800/56; A61K 2800/412; A61K 2800/5922; A61Q 17/04
See application file for complete search history.

(56) References Cited

U.S. PATENT DOCUMENTS

| | | | |
|---|---|---|---|
| 5,151,122 | A | 9/1992 | Atsumi et al. |
| 6,096,324 | A | 8/2000 | Mansouri |
| 6,120,782 | A | 9/2000 | Mansouri |
| 9,095,510 | B2 | 8/2015 | Mansouri et al. |
| 9,642,784 | B2 | 5/2017 | Mansouri et al. |
| 2002/0018797 | A1 | 2/2002 | Cui et al. |
| 2002/0086055 | A1 | 7/2002 | Wong et al. |
| 2003/0077235 | A1* | 4/2003 | Mansouri ............. A61K 8/24 424/59 |
| 2005/0031559 | A1 | 2/2005 | Cassin |
| 2005/0234114 | A1 | 10/2005 | Lee |
| 2008/0160088 | A1 | 7/2008 | Mackowiak |
| 2008/0220233 | A1 | 9/2008 | Kjellin et al. |

FOREIGN PATENT DOCUMENTS

| | | | |
|---|---|---|---|
| EP | 1837013 | A1 | 9/2007 |
| FR | 2856593 | A1 | 12/2004 |
| FR | 2857254 | A1 | 1/2005 |
| JP | S61047401 | A | 3/1986 |
| JP | S63096110 | A | 4/1988 |
| JP | H3218310 | A | 9/1991 |
| JP | H5025458 | A | 2/1993 |
| JP | H5032518 | A | 2/1993 |
| JP | H11060220 | A | 3/1999 |
| JP | 2005-47893 | A | 2/2005 |
| JP | 2009/155332 | * | 7/2009 |
| JP | 2009155332 | A | 7/2009 |
| WO | WO0047177 | A1 | 8/2000 |

OTHER PUBLICATIONS

Rigano et al., A new biologically compatible physical sunscreen with skin firming properties, Cosmetics, SOFW-Journal: 135, pp. 20-27, 2009.

* cited by examiner

*Primary Examiner* — Yanzhi Zhang
(74) *Attorney, Agent, or Firm* — Bret E. Field; Bozicevic, Field & Francis LLP

(57) ABSTRACT

Aspects of the invention include sunscreen formulations that include uniform, rigid, spherical nanoporous calcium phosphate particles. Also provided are methods of making the sunscreen formulations. The sunscreen formulations find use in sunblocking applications.

16 Claims, No Drawings

SUNSCREEN COMPOSITIONS COMPRISING UNIFORM, RIGID, SPHERICAL, NANOPOROUS CALCIUM PHOSPHATE PARTICLES AND METHODS OF MAKING AND USING THE SAME

CROSS-REFERENCE TO RELATED APPLICATIONS

Pursuant to 35 U.S.C. § 119 (e), this application claims priority to the filing date of U.S. Provisional Patent Application Ser. No. 61/259,935 filed Nov. 10, 2009; the disclosure of which application is herein incorporated by reference.

INTRODUCTION

It is well recognized that solar ultraviolet (UV) radiation poses a serious threat to human skin, which may range from the short term hazard like erythema, i.e., sunburn, to long term hazards like skin cancer and/or premature aging of the skin. UV radiation having a wavelength of 290 nm to 320 nm, generally referred to as UVB radiation, is known to cause erythema. In addition, numerous studies point to exposure of unprotected skin to UV radiation having a wavelength of from 320 nm to 400 nm, generally referred to as UVA radiation, as being the primary cause of skin cancer. It is important therefore, that skin is protected from both UVA and UVB radiations to avoid the long and short term deleterious effects of solar radiation.

The sun protection factor (SPF) rating system has been developed to help consumers select the appropriate sun protection product for any given outdoor activity involving exposure to the sun. The SPF rating corresponds to a multiplying factor by which the duration of protection by a properly applied sunscreen exceeds the exposure time that causes unprotected skin to darken. Thus, with proper application of an SPF 8 product, a person should be able to remain in the sun without skin darkening for eight times the usual unprotected duration.

In recent years, due to the increased public awareness of UV radiation hazards, the use of sun protection products has grown considerably, with consumers preferring products that have high SPF ratings and offer protection over the entire range of UV radiation, i.e., from 290 nm to 400 nm. These products typically contain certain UV-absorbers that are approved for use in sunscreen compositions by regulatory agencies (for example, US Food and Drug Administration (FDA) in the USA and COLIPA in the European Union). These approved UV-absorbers are either organic compounds, referred to in the art as organic UV-absorbers or sunscreens, or inorganic compounds, referred to in the art as inorganic UV-absorbers or sunscreens. At present, approved inorganic UV-absorbers are inorganic oxides such as titanium dioxide ($TiO_2$) and zinc oxide (ZnO). Among these inorganic oxide sunscreens, ZnO is capable of absorbing substantial amounts of UVA-radiation, and hence is often used as a UVA-sunscreen.

SUMMARY

Aspects of the invention include sunscreen formulations that include uniform, rigid, spherical nanoporous calcium phosphate particles. Also provided are methods of making the sunscreen formulations. The sunscreen formulations find use in sunblocking applications.

DETAILED DESCRIPTION

Aspects of the invention include sunscreen formulations that include uniform, rigid, spherical nanoporous calcium phosphate particles. Also provided are methods of making the sunscreen formulations. The sunscreen formulations find use in sunblocking applications.

Before the present invention is further described, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Sunscreen Formulations Comprising Uniform, Rigid, Spherical, Nanoporous Calcium Phosphate Particles Aspects of the invention include sunscreen compositions. While the SPF value of sunscreen compositions of the invention may vary, in some instances the compositions have an SPF value of 4 or more, e.g., 8 or more, 15 or more, 20 or more, 30 or more, 40 or more, 50 or more, 60 or more, including 70 or more. The compositions may have a UV-A protection value of 1 or more, such as 2 or more, e.g., 2.25 or more, etc., such as 4 or more, e.g., 8 or more, 15 or more, 20 or more, 30 or more, 40 or more, 50 or more, 60 or more, including 70 or more. SPF and UV-A protection values may be determined using any convenient protocol, such as the protocols reported in the Experimental Section, below.

As summarized above, aspects of the invention include sunscreen formulations. Sunscreen formulations of the invention include uniform, rigid, spherical, nanoporous calcium phosphate particles in a sunscreen delivery vehicle, where the sunscreen delivery vehicle may or may not include additional sunscreens, e.g., organic or inorganic sunscreens. Each of these components is now described separately in greater detail.

Uniform, Rigid, Spherical, Nanoporous Calcium Phosphate Particles

The calcium phosphate particles of the sunscreen formulations described herein are uniform, rigid, spherical, nanoporous calcium phosphate particles. By "uniform" is meant that the shape of the particles does not vary substantially, such that the particles have substantially the same spherical shape. By "rigid" is meant that the particles are hard, such that they are not pliant. The term "spherical" is employed in its conventional sense to mean a round body whose surface is at all points substantially equidistant from the center. Of interest are calcium phosphate particles in which the median diameter is 100 µm or less, such as 75 µm or less, including 50 µm or less, e.g., 25 µm or less, such as 20 µm or less, such as 10 µm or less, including 5 µm or less, where in some instances the medium diameter is 4 µm or less, such as 3 µm or less, including 2 µm or less, including 1 µm or less, including 0.1 µm or less. In a given calcium phosphate particulate composition, a distribution of diameters may be present, where in some instances the majority (such as 60% or more, 75% or more, 90% or more, 95% or more) of the particles have diameters that range from 0.01 to 20 µm, such as from 0.1 to 10 µm, and including from 0.1 to 2 µm. In some instances, the proportion of the particles that have an average particle diameter of 2 µm or less is 50% or more by number, such as 70% or more by number, including 90% or more by number. In some instances, the compositions includes two more distinct populations of particles that differ from each other in terms if diameter, e.g., where the magnitude of the difference may be 10% or more, such as 20% or more. The number of distinct population sizes may vary, and in some instances may be 2 or more, such as 3 or more, 4 or more, 5 or more, 6 or more, etc. In such embodiments, each distinct population may be present in varying amounts with respect to the total amount of calcium phosphate particles, e.g., where each distinct population is present in an amount ranging from 0.5 to 99.5% by weight, such as 1 to 75% by weight, including 1 to 50% by weight of the total weight of the calcium phosphate particles.

The particles are nanoporous. By "nanoporous" is meant that the particles have a porosity of 30% or more, such as 40% or more, including 50% or more, where the porosity may range from 30% to 85%, such as from 40% to 70%, including from 45% to 55%, as determined using a mercury intrusion porosimeter porosity determination protocol as described in ASTM D 4284-88 "Standard Test Method for Determining Pore Volume Distribution of Catalysts by Mercury Intrusion Porosimetry". Porosity is also described by "pore volume (ml/g)" and in such instances many range from 0.1 ml/g to 2.0 ml/g. In some cases, the particles have a porosity such that their internal surface area ranges from 10 $m^2/g$ to 150 $m^2/g$, such as from 20 $m^2/g$ to 100 $m^2/g$, including 30 $m^2/g$ to 80 $m^2/g$, as determined using a BET gas adsorption surface area determination protocol as described in ASTM D3663-03 Standard Test Method for Surface Area of Catalysts and Catalyst Carriers. The pore diameter may vary, ranging in certain instances from 2 to 100 nm, such as 5 to 80 nm, including 10 to 60 nm. In addition, the particles may have a tapping density ranging from 0.2 $g/cm^3$ to 0.5 $g/cm^3$, such as from 0.25 $g/cm^3$ to 0.45 $g/cm^3$, including from 0.3 $g/cm^3$ to 0.4 $g/cm^3$. The tap density can be measured by using standard ASTM WK13023—New Determination of Tap Density of Metallic Powders by a Constant Volume Measuring Method.

The particles are, in some instances, not activated with trace elements, such that they do not include amounts of trace elements such as Zn, Mn, or Mg. In some instances, the particles do no include at least partial substitution of an organic anion, e.g., lactate, for the hydroxide anion. In some instances, the particles are not apalight, i.e., the chemical formula of the particles is not $(Zn, Mn, Mg)Ca_5(PO_4)_3(OH)$ (Lactate). The particles are, in some instances, chemically pure. By chemically pure is meant that the particles are made up of substantially one type of calcium phosphate mineral. In some instances, the calcium phosphate particles are described by the molecular formula $Ca_{10}(PO_4)_6(OH)_2$.

In some instances, the particles are ceramic particles. By ceramic is meant that the particles are produced using a method which includes a step of subjecting the particles to high temperature conditions, where such conditions are illustrated below. High temperatures may range from 200 to 1000° C., such as 300 to 900° C. and including 300 to 800° C. In some embodiments, the particles have a compression rupture strength ranging from 20 to 200 MPa, such as from 50 to 150 MPa, and including 75 to 90 MPa, as determined using a SHIMADZU MCT-W500 micro-compression testing machine particle strength determination protocol with a particle sintered at temperature of 400° C. to 900° C., as described in European Patent EP1840661.

In some embodiments, the particles are biodegradable, by which is meant that the particles degrade in some manner, e.g., dissolve, over time under physiological conditions. As the particles of these embodiments are biodegradeable under physiological conditions, they at least begin to dissolve at a detectable rate under conditions of pH of 5 or less, such as 4.5 or less, including 4.3 or less. As such, the particles exhibit solubility under acidic environments of pH 5 or less, such as upon application to the skin.

The calcium phosphate particles are non-toxic, e.g., as determined via US-FDA 21 CFR Part 58, non-mutagenic, e.g., as determined by Mutagenicity Ames Test, and non-irritating, e.g., as determined via Skin Sensitization RIPT (Human).

While the uniform, rigid, spherical, nanoporous calcium phosphate particles of the sunscreen compositions may vary in a variety of different parameters, including as reviewed above, in some embodiments the particles employed in the sunscreen compositions are chemically pure particles that have a mean diameter of 2 µm.

The uniform, rigid, spherical, nanoporous calcium phosphate particles of the sunscreen compositions of the invention may be prepared using any convenient protocol.

Examples of fabrication protocols of interest include, but are not limited to, those described in U.S. Pat. Nos. 4,781,904; 5,039,408; 5,082,566; and 5,158,756; the disclosures of which are herein incorporated by reference. In one protocol of interest, the particles are manufactured by spray drying a slurry that includes nano calcium phosphate (e.g., hydroxyapatite) crystals (which may range from 2 nm to 100 nm size range) to produce uniform spherical nanoporous calcium phosphate particles. The resultant particles are then sintered for a period of time sufficient to provide mechanically and chemically stable rigid spheres. In this step, the sintering temperatures may range from 200° C. to 1000° C., such as 300° C. to 900° C. and including 300° C. to 800° C. for a period of time ranging from 1 hour to 10 hours, such as 2 hours to 8 hours and including 3 hours to 6 hours. Additional details regarding this method of manufacturing the uniform, rigid, spherical, nanoporous calcium phosphate particles are provided in U.S. Provisional Application Ser. No. 61/108,805, the disclosure of which is herein incorporated by reference.

Where desired, initially porous particles, e.g., as described above, may be rendered non-porous prior to combination with the sunscreen delivery vehicle in preparing the sunscreen compositions. Accordingly, in some instances the calcium phosphate particles present in the sunscreen compositions are non-porous. In these embodiments, initially porous particles may be combined with a suitable filler, e.g., an inert filler, so that the porosity of the pores is reduced by a desired amount. In such applications, loading protocols described in copending application Ser. No. 12/565,687 (the disclosure of which is herein incorporated by reference), may be employed.

In addition, as further described below, the particles may also be loaded with one or more components of the sunscreen composition, e.g., organic or inorganic sunscreen blocking agents, antioxidants, etc.

Sunscreen Delivery Vehicle

Sunscreen compositions of the invention include a suitable amount of the above described particles present in a sunscreen delivery vehicle (i.e., topical delivery vehicle) that is configured for application to a topical site of a living subject, such as a human. As such, sunscreen compositions of the invention are compositions that are formulated for application to a keratinized skin surface of a mammalian subject, such as a human subject. By keratinized skin surface is meant a skin location of a subject, i.e., a location of the external covering or integument of an animal body. Because the topical compositions of the invention are formulated for delivery to topical location, they are formulated so as to be physiologically compatible with the topical location for which they are formulated. Accordingly, when contacted with the target keratinized skin surface for which they are formulated, the topical compositions do not cause substantial, if any, physiological responses (such as inflammation or irritation) that would render the use of the topical compositions unsuitable for topical application.

As indicated above, the sunscreen compositions include an amount of uniform, rigid, spherical nanoporous calcium phosphate particles, e.g., as described above. In a given sunscreen composition, a distribution of diameters for the particles thereof may be present, where in some instances the majority (such as 60% or more, 75% or more, 90% or more, 95% or more) of the particles have diameters that range from 0.01 to 20 μm, such as 0.05 to 15 μm such as from 0.1 to 10 μm, and including from 0.1 to 2 μm. In some instances, the proportion of the particles that have an average particle diameter of 2 μm or less is 50% or more by number, such as 70% or more by number, including 90% or more by number. In some instances, formulations are manufactured to include two or more, including 3 or more, 4 or more, 5 or more, etc., discrete particle size populations, where each particle size population has a different average particle size. For example, a composition may include a first particle size population having an average particle size ranging from 0.1 to 2 μm and a second particle size population having an average particle size ranging from 2 to 20 μm. Where two or more different particle size populations are present, the difference in average particle size between any two particle size populations may vary, and in certain embodiments is 1 μm or greater, such as 2 μm or greater, including 3 μm or greater, 5 μm or greater, and 10 μm or greater.

The total amount of a particles that is present in a given sunscreen composition and therefore combined with a sunscreen delivery vehicle may vary. In some instances, the total amount of calcium phosphate particles present in the composition is sufficient to increase the SPF factor of the composition as compared to a control (i.e., the same formulation lacking the calcium phosphate particles) by a magnitude of 1 or more, such as 2 or more, e.g., 3 or more, 4 or more, 5 or more, 6 or more, 7 or more, 8 or more, 9 or more, 10 or more, where in some instances the magnitude increase in SPF factor ranges from 0.5 to 5, such as 1 to 4, e.g., 2 to 3. In some instances, the total amount of calcium phosphate particles present in the composition is sufficient to increase the UV-A protection value of the composition as compared to a control (i.e., the same formulation lacking the calcium phosphate particles) by a magnitude of 0.1 or more, such as 0.2 or more, e.g., 0.3 or more, 0.4 or more, 0.5 or more, 0.6 or more, 0.7 or more, 0.8 or more, 0.9 or more, 1.0 or more. In some embodiments, the amount of particles present in the delivery vehicle ranges from 0.01 to 200 mg/g, such as 0.1 to 100 mg/g and including 1 to 50 mg/g active agent loaded particles per gram of delivery vehicle. In certain embodiments the particles are present in compositions in an amount ranging from about 0.001 to about 80% by weight, such as from about 0.01 to about 70% by weight, and including from about 0.05 to about 60% by weight, e.g., 0.1 to 10% by weight, such as 0.1 to 5% by weight, including 1% by weight.

As indicated above, the sunscreen compositions of the invention further include a sunscreen delivery vehicle. The sunscreen delivery vehicle (i.e., topical delivery component) refers to that portion of the sunscreen composition that is not the calcium phosphate particles, where this portion of the sunscreen composition may include a number of different and varying components, as reviewed below. Sunscreen delivery vehicles of interest include vehicles formulated for application to a topical region or surface of a subject, such as a keratinized skin surface. The subject compositions may be formulated as stable solutions or suspensions of the components, e.g., in an aqueous solvent. Where desired, the components may be combined with one or more carrier materials to form a solution, suspension, gel, lotion, cream, ointment, aerosol spray or the like, as desired. In some instances, the sunscreen delivery vehicle is an oil-in-water or water-in-oil emulsion composition.

Sunscreen delivery vehicles of interest include, optionally, one or more additional sunscreens and a carrier.

Additional Sunscreens

In some instances, the sunscreen composition of the invention may include an amount of an additional sunscreen component, e.g., UV absorber or UV scatterer, which may be inorganic or organic. The additional sunscreen component (such as UV absorber) may absorb and/or physically block UV-B radiation, e.g., UV-B and/or both UV-A radiation. In some instances, one or more additional sunscreen components may be present in type and amount that provides for more UV-B screening than UV-A screening, e.g., in compositions configured or formulated to provide for the occurrence of a "natural" tan. In some instances, the sunscreen compositions of the present invention will be effective against both UV-A and UV-B and have either strong UV-A/UV-B sunblock actives or the presence of an additional UV-A sunblock active, e.g., to provide a balanced UV-A/UV-B blocking composition. Of interest are inorganic actives that work by reflecting the UV light and organic actives that work, predominately, by absorbing UV energy. The amount of the sunblock active to be incorporated into the sunscreen formulations, when present, may vary.

Organic sunscreen components of interest include, but are not limited to, avobenzone, butyl methoxydibenzoylmethane, cinoxate, benzophenone-8, dioxybenzone, homosalate, octylsalate, menthyl anthranilate, octocrylene, ethyhexyl methoxycinnamate, octyl methoxycinnamate, octyl salicylate, oxybenzone, padimate O, ethylhexyl salicylate, benzophenone-3, p-aminobenzoic acid (PABA), ethylhexyl dimethyl PABA, glyceryl PABA, phenylbenzimidazole sulfonic acid, sulfisobezone, trolamine salicylate, 4-methylbenzylidene camphor, bisoctrizole, bemotrizinol, ecamsule, drometrizole trisiloxane, disodium phenyl dibenzimidazole tetrasulfonate, diethylamine hydroxybenzoyl hexyl bezoate, octyl triazone, hexyl benzoate, benzophenone-4, ethyhexyl triazone, diethylhexyl butamido triazone, bisimidazylate, polysilicone-15, 2-ethylhexyl 2-cyano-3,3-diphenyl-2-propenoate (octrocrylene), etc.

Inorganic sunscreens of interest include, but are not limited to, titanium oxide, e.g., microfine surface treated titanium dioxide, and zinc oxide, e.g., microfine untreated and surface treated zinc oxide. The titanium dioxide in the sunscreen compositions may have a mean primary particle size of between 5 and 150 nm, preferably between 10 and 100 nm. Titanium oxide may have an anatase, rutile, or amorphous structure. The zinc oxide in the sunscreen compositions preferably has a mean primary particle size of between 5 nm and 150 nm, preferably between 10 nm and 100 nm.

In some instances, the sunscreen compositions of the present invention will comprise a combination of such sunblock actives. As such, in some instances the sunscreen composition include, in addition to the calcium phosphate particles described above, combinations of both inorganic and organic sunscreen components. In some instances, the sunscreen components are chosen from the following list of agents: p-aminobenzoic acid (PABA); padimate O (OD-PABA, octyldimethyl-PABA, σ-PABA); phenylbenzimidazole sulfonic acid (Ensulizole, Eusolex 232, PBSA, Parsol H); cinoxate (2-Ethoxyethyl p-methoxycinnamate), dioxybenzone (Benzophenone-8), oxybenzone (Benzophenone-3, Eusolex 4360, Escalol 567), homosalate (Homomethyl salicylate, HMS), menthyl anthranilate (Meradimate), octocrylene (Eusolex OCR, 2-cyano-3,3diphenyl acrylic acid, 2-ethylhexylester), octylmethoxycinnamate (Octinoxate, EMC, OMC, Ethylmethoxycinnamate, Escalol 557, 2-ethylhexyl-paramethoxycinnamate, Parsol MCX), octyl salicylate (Octisalate, 2-Ethylhexyl salicylate, Escalol 587), sulisobenzone (2-Hydroxy-4-Methoxybenzophenone-5-sulfonic acid, 3-benzoyl-4-hydroxy-6-methoxybenzenesulfonic acid, Benzophenone-4, Escalol 577), trolamine salicylate (Triethanolamine salicylate), avobenzone (1-(4-methoxyphenyl)-3-(4-tert-butylphenyl)propane-1,3-dione, Butyl methoxy dibenzoylmethane, BMDBM, Parsol 1789, Eusolex 9020), ecamsule (Mexoryl SX, Terephthalylidene Dicamphor Sulfonic Acid), titanium dioxide, zinc oxide, 4-methylbenzylidene camphor (Enzacamene, Parsol 5000, Eusolex 6300, MBC), tinosorb M (Bisoctrizole, Methylene Bis-Benzotriazolyl Tetramethylbutylphenol, MBBT), tinosorb S (Bis-ethylhexyloxyphenol methoxyphenol triazine, Bemotrizinol, BEMT, anisotriazine), neo heliopan AP (Bisdisulizole Disodium, Disodium phenyl dibenzimidazole tetrasulfonate, bisimidazylate, DPDT), mexoryl XL (Drometrizole Trisiloxane), benzophenone-9 (Uvinul DS 49, CAS 3121-60-6, Sodium Dihydroxy Dimethoxy Disulfobenzophenone), uvinul T 150 (Octyl triazone, ethylhexyl triazone, EHT), uvinul A plus (Diethylamino Hydroxybenzoyl Hexyl Benzoate), uvasorb HEB (Iscotrizinol, Diethylhexyl butamido triazone, DBT), parsol SLX (Dimethico-diethylbenzalmalonate, Polysilicone-15), isopentenyl-4-methoxycinnamate (Isoamyl p-Methoxycinnamate, IMC, Neo Heliopan E1000, Amiloxate)

The amounts of sunscreens which are employed in any given composition will vary, e.g., depending upon the sunscreen chosen and the desired Sun Protection Factor (SPF) to be achieved.

Carrier

The sunscreen delivery vehicles include a carrier, which is that component of the vehicle which is not the inorganic or organic sunscreen components, e.g., as described above (it is noted that in those instances where the vehicle does not include an additional sunscreen component, the carrier and the vehicle are the same, such that the carrier is not a component of the vehicle but is the entire vehicle). The carrier is that material or combination of materials that is used to essentially carry or deliver the calcium phosphate particles, sunblock active(s) when present) to the skin. The specific carrier material that is present in a given sunscreen composition will depend upon the desired delivery method for the composition, e.g., spray one, rub on, etc. For example, as mentioned earlier, the sunscreen compositions may be in the form of lotions, creams, gels, foams, emulsions, dispersions, sprays, liposomes, coacervates, etc. Each composition may include any convenient topical excipient and like agents desirable for achieving the particular form. Of interest are carriers that include an amount of water, e.g., 30% by weight or more, such as 40% by weight or more. Excipients of interest may include, e.g., mineral oils and emulsifying agents. In its most simplest of embodiments, the carrier may be water, alcohol or water/alcohol combinations, or other solvent(s) or solvent systems in which the aforementioned actives may be, e.g., soluble, dispersed, emulsified, etc. In some instances, sunscreen compositions of interest will include excipients and the like that create a substantially stable, homogenous sunscreen composition and/or provide body and viscosity to the sunscreen composition so that the actives do not merely run off the skin once applied. In some instances, the carrier will comprise from 30 to 99% by weight of the sunscreen composition. Any known carrier or base composition may be present in the sunscreen compositions of the invention. Suitable carriers and carrier compositions of interest include, but are not limited to: those described in U.S. Pat. Nos. 7,186,404; 7,175,834; 7,172, 754; 7,175,835; 7,101,536; 7,078,022; 5,175,340; 5,567, 418, 5,538,716; 5,951,968; 5,670,140; 6,831,191; 6,602, 515; 7,166,273; 6,936,735; 6,699,463; 6,165,450; 7,150, 876; 6,962,692; 5,830,441.

Though a carrier by itself is sufficient, the sunscreen compositions may contain various other components typically associated with skin care products. For example, various skin care agents including, but not limited to, skin care excipients as well as additional photoprotective agents and skin lightening agents may be present. Such agents include, but are not limited to antioxidants, vitamins, anti-inflammatory agents, self-tanning agents, moisturizers, emollients, humectants, and the like, and mixtures thereof, in their conventional amounts. Agents and additive materials of interest include those described in U.S. Pat. No. 7,078,022.

Suitable antioxidants include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate, ascorbyl polypeptide and ascorbyl phosphate). Oil-soluble antioxidants suitable for use in the compositions of this invention include, but are not limited to, butylated hydroxytoluene, retinoids (e.g., retinol and retinyl palmitate), tocopherols (e.g., tocopherol acetate), sodium tocopheryl phosphate, tocotrienols, alkyl-resorcinols, curcurmin and its derivatives and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, Phyllanthus emblica and propolis. Other examples of antioxidants may be found on pages 1612-13 of the ICI Handbook as well as in U.S. Pat. No. 6,124,268.

The sunscreen compositions of the present invention may also include one or more vitamins and/or their derivatives. Vitamins and vitamin derivatives include, for example, vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C and derivatives (for example ascorbyl palmitate, magnesium ascorbyl phosphate, ascorbyl acetate), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$). Preferred vitamins are, for example, vitamin A palmitate, vitamin C and derivatives thereof, DL-α-tocopherol, tocopherol E acetate, nicotinic acid, pantothenic acid and biotin.

Suitable emollients include those agents known for softening the skin which may be selected from hydrocarbons, fatty acids, fatty alcohols, e.g., cetyl alcohol and stearyl alcohol, and esters. Petrolatum is a common hydrocarbon type of emollient conditioning agent. Other hydrocarbons that may be employed include alkyl benzoate, mineral oil, polyolefins such as polydecene, and paraffins, such as iso-hexadecane. Fatty acids and alcohols typically have from about 10 to 30 carbon atoms. Illustrative are myristic, isostearic, hydroxystearic, oleic, linoleic, ricinoleic, behenic and eruicic acids and alcohols. Oily ester emollients may be those selected from one or more of the following, triglyceride esters, acetoglyceride esters, ethoxylated glycerides, all esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylic/capric triglycerides, siloxanes, e.g., cyclotetrasiloxane and cyclopentasiloxane, propylene glycol dicaprylate/dicaprate and decyl oleate.

Suitable humectants include various polyhydric alcohols, especially polyalkylene glycols and, more preferably, alkylene polyols and their derivatives. Exemplary humectants include propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol; glycerin, ethoxylated glycerin, propoxylated glycerin, compatible solutes, such as ectoin, hydroxectoin, taurines, carnithine, acetyl carnithine and mixtures thereof. Also of interest are urea; guanidine; glycolic acid and glycolate salts (e.g. ammonium and quaternary alkyl ammonium); lactic acid and lactate salts (e.g. sodium, ammonium, and quaternary alkyl ammonium); aloe vera in any of its variety of forms (e.g., aloe vera gel); pyrrolidone carboxylic acids and their salts (e.g., sodium pyrrolidone carboxylic acid); sugars and starches; sugars and starches and their derivatives (e.g., honey extract, alkoxylated glucose); 6-(N-acetylamino)-4-oxahexyltrimonium chloride; hyaluronic acid; chitin, lactamide monoethanolamine; acetamide monoethanolamine; propoxylated glycerol; etc. In some instances, humectants of interest include, but are not limited to: $C_3$-$C_6$ diols and triols, such as the $C_3$-$C_6$ diols and triols selected from the group consisting of propylene glycol, 1,3-dihydroxypropane, glycerin, urea; honey extract, butylene glycol, hexylene glycol, 1,4-dihydroxyhexane, 1,2,6-hexanetriol, and mixtures thereof. In some instances, the humectants are those selected from the group consisting of glycerin, urea, honey extract, butylene glycol, hexylene glycol, and mixtures thereof. When employed in effective amounts, generally from 1 to 30%, preferably from 2 to 20%, by weight of the sunscreen composition, these additives serve as skin moisturizers as well as reduce scaling and stimulate the removal of built-up scale from the skin.

In some instances, the compositions include one or more skin conditioning agents, where skin conditioning agents of interest include occlusive skin condition agents, emollient skin conditioning agents and miscellaneous skin conditioning agents, as well as combinations thereof.

Occlusive skin conditioning agents of interest include, but are not limited to: Avena sativa (oat) kernel oil, behenyl isostearate, caprylic/capric triglyceride, caprylic/capric/myristic/stearic triglyceride, caprylyl methicone, caprylyl trimethicone, safflower seed oil, cetyl palmitate, cetyl stearate, coconut oil, dimethicone PEG-8 olivate, emu oil, glycol distearate, hydrogenated avocado oil, hydrogenated rice bran oil, propylene glycol diisstearate, sweet almond oil, jojoba oil, squalane, stearyl beewax, stearyl dimethicone, cocoa seed butter, wheat germ oil, vegetable oil, etc.

Also of interest as skin conditioning agents are emollients. The compositions may include one or more emollients, which typically act to soften, soothe, and otherwise lubricate and/or moisturize the skin. Suitable emollients that can be incorporated into the compositions include, but are not limited to: oils such as petrolatum based oils, petrolatum, vegetable based oils, mineral oils, natural or synthetic oils, alkyl dimethicones, alkyl methicones, alkyldimethicone copolyols, phenyl silicones, alkyl trimethylsilanes, dimethicone, dimethicone crosspolymers, cyclomethicone, cyclotetrasiloxane, cyclopentasiloxane, lanolin and its derivatives, fatty esters, glycerol esters and derivatives, propylene glycol esters and derivatives, alkoxylated carboxylic acids, alkoxylated alcohols, fatty alcohols, and combinations thereof. Suitable esters could include, but not be limited to, cetyl palmitate, stearyl palmitate, cetyl stearate, isopropyl laurate, isopropyl myristate, isopropyl palmitate, glyceryl caprylate and combinations thereof. The fatty alcohols could include but not be limited to octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients.

Also of interest are miscellaneous skin conditioning agents. Examples of miscellaneous skin conditioning agents of interest include, but are not limited to: alanine, algae extract, allantoin, aloe vera extract, aluminum PCA, apricot kernel amino acids, arbutin, arginine, asorbic acid, bisabolol, biotin, caffeine, calcium ascorbate, calendula oil, carnitine, carnosine, lime oil, orange oil, grapefruit oil, cucumber extract, tumeric extract, carrot seed oil, dipalmitoyl glutathione, dipalmitoyl hydroxyproline, dipotassium glycyrrhizate, disodium adenosine phosphate, disodium adenosine triphosphate, elastin; fennel extract, ginko biloba extract, beta-glucan, glutamine, glycolipids, glycerrhizic acid, histidine, hyaluronic acid, hydrogenated polydecene, hydrolyzed algae extract, hydrolyzed collagen, hydrolyzed DNA, hydrolyzed oat protein, kinetin, lactic acid, linoleic acid, lysine, magnesium ascorbate, niacin, oat amino acids, oligopeptide-5, oligopeptide-6, oligopeptide-10, palmitoyl oligopeptide, papain, pea extract, sweet almond oil, apple extract, retinyl palmitate, resveratrol, soluble collagen, etc.

In some instances, the compositions include an emulsifying agent. Emulsifying agents of interest include, but are not limited to, sorbitan esters, glyceryl esters, polyglyceryl esters, methyl glucose esters, sucrose esters, ethoxylated fatty alcohols, hydrogenated castor oil ethoxylates, sorbitan ester ethoxylates, polymeric emulsifiers, silicone emulsifiers, glyceryl monoesters, preferably glyceryl monoesters of $C_{16}$-$C_{22}$ saturated, unsaturated and branched chain fatty acids such as glyceryl oleate, glyceryl monostearate, glyceryl monopalmitate, glyceryl monobehenate, and mixtures thereof; polyglyceryl esters of $C_{16}$-$C_{22}$ saturated, unsaturated and branched chain fatty acids, such as polyglyceryl-4 isostearate, polyglyceryl-3 oleate, diglycerol monooleate, tetraglycerol monooleate and mixtures thereof; methyl glucose esters, preferably methyl glucose esters of $C_{16}$-$C_{22}$ saturated, unsaturated and branched chain fatty acids such as methyl glucose dioleate, methyl glucose sesquiisostearate, and mixtures thereof; sucrose fatty acid esters, preferably sucrose esters of $C_{12}$-$C_{22}$ saturated, unsaturated and branched chain fatty acids such as sucrose stearate, sucrose trilaurate, sucrose distearate, $C_{12}$-$C_{22}$ ethoxylated fatty alcohols such as oleth-2, oleth-3, steareth-2, and mixtures thereof; hydrogenated castor oil ethoxylates such as PEG-7 hydrogenated castor oil; sorbitan ester ethoxylates such as PEG-40 sorbitan peroleate, polysorbate-80, and mixtures thereof; polymeric emulsifiers such as ethoxylated dodecyl glycol copolymer; and silicone emulsifiers such as laurylmethicone copolyol, cetyldimethicone, dimethicone copolyol, and mixtures thereof. (e.g. apricot kernel oil PEG-6 esters, beeswax, behenoyl stearic acid, ceteareth-2, cetearyl glucoside, cetyl alcohol, cetyl phosphate, glyceryl palmitate, glyceryl caprylate, glyceryl stearate, hydrogenated lecithin, hydrolyzed beeswax, isostearyl glucoside, palmitic acid, palm kernel acid, glyceride, PEG-20 stearate, PEG-100 stearate, oleic acid, stearic acid, stearyl alcohol, stearyl phosphate, sucrose cocoate, sucrose palmitate, sucrose stearate, TEA stearate, tocopheryl phosphate, wheat germ oil PEG-8 esters, xanthan gum, corn oil), etc.

The compositions of the disclosure can also include natural fats and oils. As used herein, the term "natural fat or oil" is intended to include fats, oils, essential oils, essential fatty acids, non-essential fatty acids, phospholipids, and combinations thereof. These natural fats and oils can provide a source of essential and non-essential fatty acids to those found in the skin's natural barrier. Suitable natural fats or oils can include citrus oil, olive oil, avocado oil, apricot oil, babassu oil, borage oil, camellia oil, canola oil, castor oil, coconut oil, corn oil, cottonseed oil, emu oil, evening primrose oil, hydrogenated cottonseed oil, hydrogenated palm kernel oil, jojoba oil, maleated soybean oil, meadowfoam oil, palm kernel oil, peanut oil, rapeseed oil, grapeseed oil, safflower oil, sphingolipids, sweet almond oil, tall oil, lauric acid, palmitic acid, stearic acid, linoleic acid, stearyl alcohol, lauryl alcohol, myristyl alcohol, behenyl alcohol, rose hip oil, calendula oil, chamomile oil, eucalyptus oil, juniper oil, sandlewood oil, tea tree oil, sunflower oil, soybean oil, and combinations thereof. The composition of the invention may include fats and oils in an amount of from about 0.01% (by weight of the composition) to about 40% (by weight of the composition), such as from about 0.05% (by weight of the composition) to about 25% (by weight of the composition), and including from about 0.1% (by weight of the composition) to about 10% (by weight of the composition).

Suitable preservatives for use in the formulation of the present invention include, but are not limited to, one or more of phenoxyethanol, ethylhexylglycerin; caprylyl glycol, sorbic acid, sodium hydroxymethylglycinate, disodium salt of ethylenediaminetetraacetic acid, chloroxylenol, sodium benzoate, DMDM Hydantoin, 3-iodo-2-propylbutyl carbamate, potassium sorbate, chlorhexidine digluconate, the alkyl esters of para-hydroxybenzoic acid (the parabens, e.g. butylparaben, methylparaben and propylparaben), *Lonicera caprifolium* (honeysuckle) flower extract & *Lonicera japonica* (honeysuckle) flower extract.

Examples of anti-inflammatory ingredients include, but are not limited to, bisabolol, curcurmin and its derivatives, retinoids, flavonoids and other polyphenolics etc. These and other anti-inflammatory agents, as well as additional antioxidants and the like, are disclosed—US 2005/0048008A1.

Examples of self-tanning ingredients include, but are not limited to, dihydroxyacetone and erythrulose.

The sunscreen compositions of the present invention may also include one or more skin penetrants. These are additives that, when applied to the skin, have a direct effect on the permeability of the skin barrier: increasing the speed with which and/or the amount by which certain other compounds are able to penetrate into the skin layers. Exemplary organic penetration enhancers include dimethyl sulfoxide; isopropyl myristate; decyl, undecyl or dodecyl alcohol; propylene glycol; polyethylene glycol, $C_{9-11}$, $C_{12-13}$ or $C_{12-15}$ fatty alcohols; none; alkyl pyrrolidones; lecithin; etc. Surfactants can also be used as penetration enhancers.

Other optional adjunct ingredients for the sunscreen compositions of the present invention include preservatives, waterproofing agents, fragrances, anti-foam agents, plant extracts (Aloe vera, witch hazel, cucumber, etc), opacifiers, stabilizers, skin conditioning agents colorants, and the like, each in amounts effective to accomplish their respective functions.

The carrier may also contain other physiologically acceptable excipients or other minor additives, particularly associated with organoleptic properties, such as fragrances, dyes, buffers, cooling agents (e.g. menthol), stabilizers or the like. The excipients and minor additives will be present in conventional amounts, e.g., ranging from about 0.001% to 5%, such as 0.001-2%, by weight, and in some instances not exceeding a total of 10% by weight.

Loaded Calcium Phosphate Particles

Where desired, the calcium phosphate particles may be loaded with an amount of one or more of the above components, e.g., anti-oxidants, UV absorbers/blockers, etc. In such applications, loading protocols described in co-pending application Ser. No. 12/565,687 (the disclosure of which is herein incorporated by reference), may be employed.

Emulsion Formulations

As indicated above, in some instances the sunscreen compositions are emulsions, e.g., wherein the emulsion may be oil-in-water or water-in-oil emulsion compositions. Of interest are oil-in-water emulsified sunscreen compositions that include by weight:

(a) from 0.001% to 10% of Uniform Rigid Spherical Nanoporous Calcium Phosphate Particles as an ultra violet (UV) blocking and scattering agent, e.g., as described above;

(b) from about 0.1% to about 50% of inorganic sunscreen component (e.g., UV shielding particles) such as described above;

(c) from about 0.1% to about 15% of organic sunscreen component (e.g., UV absorbers) such as described above;

(d) from about 0.1% to about 10% of solid wax or polymer film former for the water proof function;

(e) 30% or more of the entire composition of a lipophilic component (e.g., made up of fats, oils, other lipophilic ingredients, etc.), e.g., as described above;

(f) from 30 to 80%, such as 40 to 50% water.

In some instances, the above formulation includes one or more of the following additional components:

(g) From about 0.01% to about 10% of Skin Conditioning Agent—Miscellaneous: Ex: Botanivera 1-200 C (INCI:Aloe barbadensis Leaf Juice);

(h) One or more viscosity enhancers (e.g Xanthan Gum) in an amount of from about 0.01% (by weight of the composition) to about 25% (by weight of the composition), such as from about 0.05% (by weight of the composition) to about 10% (by weight of the composition), and including from about 0.1% (by weight of the composition) to about 5% (by weight of the composition);

(i) From about 0.5% to about 25% of Humectant: e.g., Glycerin;

(j) From about 0.5% to about 20% of Skin Conditioning Agent—Occlusive: e.g., (INCI:Caprylic/Capric Triglyceride); Caprylyl Trimethicone;

(k) From about 0.01% to about 20% of Emulsifier and emulsion stabilizer: e.g. Lipomulse 165 (INCI: Glyceryl Stearate & PEG-100 Stearate); Capmul 708 G (Glyceryl Caprylate); Cetyl Alcohol; Stearyl Alcohol;

(l) From about 0.5% to about 25% of Skin Conditioning agent—Emollient: e.g., Capmul 708 G (Glyceryl Caprylate); Botanisil CM-70 (Cyclotetrasiloxane and Cyclopentasiloxane); Botanisil GB-20 (INCI:Cyclopentasiloxane & Dimethicone/Vinyl Dimethicone Crosspolymer;

(m) From about 0.5% to about 5% of Skin Conditioning Agent Viscosity Increasing agent—nonaqueous: e.g., Botanisil GB-20 (INCI:Cyclopentasiloxane & Dimethicone/Vinyl Dimethicone Crosspolymer);

(n) From about 0.5% to about 1.1% of Preservative: e.g., Euxyl PE 9010 (INCI: Phenoxyethanol & Ethylhexylglycerin);

(o) From about 0.001% to about 10% of Antioxidant; Skin Conditioning Agent—Miscellaneous; e.g., Sodium Tocopheryl Phosphate; Tocopheryl Acetate (p) From about 0.01% to about 10% of Skin Conditioning Agent—Miscellaneous; Viscosity Increasing Agent—Aqueous; e.g., Hyaluronic Acid Container In some instances, the sunscreen composition is present in container. The container may be configured to hold a desired amount of sunscreen and provide for storage stability of the sunscreen. In some instances, the container is configured to contain from 0.5 to 100 oz of sunscreen composition, such as 1 to 50 oz of sunscreen composition.

As such, aspects of the invention include a container delimiting at least one compartment, the container being closed by means of a closing member; and a composition as described above and placed inside said compartment. The container may be in any appropriate form. It may in particular be in the form of a bottle, a tube, a jar, a case, a box, a sachet or a carton. The closing member may be in the form of a removable stopper, a lid, a cap, a tear-off strip or a capsule, in particular of the type comprising a body attached to the container and a cover cap articulated on the body. It may also be in the form of a member for selectively closing the container, in particular a pump, a valve or a flap valve. The product may be contained directly in the container, or indirectly. By way of example, the product may be arranged on an impregnated carrier, in particular in the form of a wipe or of a pad, and arranged (individually or in plurality) in a box or in a sachet. Such a carrier incorporating the product is described, for example, in WO 01/03538. The closing member may be coupled to the container by screwing. Alternatively, the coupling between the closing member and the container is done other than by screwing, in particular via a bayonet mechanism, by click-fastening, gripping, welding, bonding or by magnetic attraction. The term "click-fastening" is in particular intended to mean any system involving the crossing of a bead or cord of material by elastic deformation of a portion, in particular of the closing member, followed by return to the elastically unconstrained position of said portion after the crossing of the bead or cord. The container may be at least partially made of thermoplastic material. By way of examples of thermoplastic materials, mention may be made of polypropylene or polyethylene. Alternatively, the container is made of non-thermoplastic material, in particular of glass or of metal (or alloy). The container may have rigid walls or deformable walls, in particular in the form of a tube or of a tubular bottle. The container may comprise means for distributing or facilitating the distribution of the composition. By way of example, the container may have deformable walls so as to cause the composition to exit in response to a positive pressure inside the container, this positive pressure being caused by elastic (or non-elastic) squeezing of the walls of the container.

Fabrication Methods

Aspects of the invention further include methods of making the sunscreen formulations that include the uniform, rigid, spherical, nanoporous calcium phosphate particles and topical compositions that include the same. With respect to methods of making the formulations, aspects of these methods include combining an amount of uniform, rigid, spherical, nanoporous calcium phosphate particles comprising a porous structure that defines an internal space; and a desired sunscreen delivery vehicle.

Utility and Methods

The sunscreen compositions of the invention find use in a variety of different application, including sunblocking applications. The compositions are effective in reducing or preventing skin damage due to UV exposure, such as exposure to the sun. As such, aspects of the invention include methods of protecting skin from damage due to UV exposure, where the methods include the step of applying sunscreen compositions according to embodiments of the invention to skin. In some instances, the present invention provides a method of reducing or preventing erythema resulting from exposure to UV light. Methods of the invention may include applying the sunscreen composition to areas of the skin that are or may be exposed to the sun. In some instances, the sunscreen composition is applied to areas that are not typically exposed to the sun but that nevertheless have exposure to the penetrating UV rays. For example, tee shirts and other light fabrics offer minimal protection against sun exposure, especially to UV rays. Thus, in some instances the sunscreen compositions may be applied to essentially all areas of the body, including those typically covered by clothing.

The amount of the sunscreen composition that is to be applied to the skin may vary, so long as it is sufficient to provide the desired sun protection. To some extent, the amount depends upon the form of the sunscreen composition and its mode of application. For example, a spray formulation may be applied so as to provide a light, even coat on the skin. Lotions, creams, gels and the like may be applied at a rate of about 1 to 2 ounces for the entire body, i.e., for the exposed skin of a "average individual" wearing a swimsuit and standing 5 feet 4 inches tall, weighing 150 pounds, and having a 32 inch waist. This translates to an application rate of about 2 mg/cm$^2$ of skin. On the face, an application rate of interest is ¼ to ⅓ of a teaspoon. In some instances, the application rate will be from about 0.1 to about 10 mg/cm$^2$, preferably from about 1 to about 3 mg/cm$^2$, of skin.

In certain embodiments, the sunscreen composition is applied before sun exposure, such as at least 15 minutes before, and reapplied every 2 hours or more frequently, e.g., if the individual engages in activities/actions that may cause the sunscreen composition to wear or wipe off, e.g., swimming; washing dishes, windows, etc., washing hands and/or face; contact sports activities; activities that promote substantial sweating; etc.

In addition to the above-mentioned photo-protective benefits of the sunscreen compositions, the continual, e.g., daily, use of the sunscreen compositions of the present invention, regardless of whether one anticipates UV exposure or not, provides in some instances a number of additional benefits to skin. For example, the continual use of these sunscreen compositions may delay the appearance of fine lines, enhance extracellular matrix cohesion, reduce the appearance of spider veins, improving skin firmness and elasticity: skin effects that are not only a result of exposure to the sun but also the natural aging process. For example, the long-term use of the inventive sunscreen compositions may help with thickening the keratinous tissue (i.e., building the epidermis and/or dermis layers of the skin), thereby preventing and/or retarding atrophy of human skin; preventing and/or retarding the appearance of spider veins and/or red blotchiness on human skin; preventing and/or retarding the appearance of dark circles under the eye; preventing and/or retarding sallowness and/or sagging of human skin; soften and/or smooth lips; preventing and/or relieving itch of human skin, regulating skin texture (e.g. wrinkles and fine lines), improving skin color (e.g. redness, freckles); and the like.

The following examples are offered by way of illustration and not by way of limitation.

EXPERIMENTAL

I. Formulations

The following formulas were prepared. Formula 10090 lacks calcium phosphate particles and formulation 10091 includes an amount of calcium phosphate particles.

| Raw Material | % w/w | Function |
|---|---|---|
| LSC.RNB010091 | | |
| Purified Water | 47.325% | Skin Conditioning Agent - Miscellaneous; Solvent |
| Botanivera 1-200C (INCI: *Aloe barbadensis* Leaf Juice) | 0.100% | Skin Conditioning Agent - Miscellaneous |
| Xanthan Gum | 0.400% | Viscosity Increasing Agent - Aqueous; Binder; Emulsion stabilizer |
| Glycerin | 8.000% | Humectant |
| Neo Heliopan ® 303 (INCI: Octocrylene) | 6.000% | Sunscreen agent |
| Ethylhexyl Salicylate | 1.600% | Sunscreen agent |
| TiO2 (INCI: Titanium Dioxide) | 1.750% | Sunscreen agent |
| Zinc Oxide | 6.000% | Sunscreen agent |
| CCT (INCI: Caprylic/Capric Triglyceride) | 7.000% | Skin Conditioning Agent - Occlusive |
| Lipomulse 165 (INCI: Glyceryl Stearate & PEG-100 Stearate) | 2.500% | Emulsifier and emulsion stabilizer |
| Capmul 708 G (INCI: Glyceryl Caprylate) | 3.000% | Skin Conditioning agent - Emollient: Surfactant - Emulsifying agent |
| Cetyl Alcohol | 2.000% | Emulsion stabilizer; Opacifying Agent; Surfactant Emulsifying Agent |
| Stearyl Alcohol | 2.000% | Emulsion stabilizer; Opacifying Agent; Surfactant Emulsifying Agent |
| Botanisil CM-70 (INCI: Cyclotetraxsiloxane and Cyclopentasiloxane) | 5.000% | Skin Conditioning Agent - Emollient |
| Botanisil GB-20 (INCI: Cyclopentasiloxane & Dimethicone/Vinyl Dimethicone Crosspolymer) | 2.000% | Skin Conditioning Agent - Emollient & Viscosity Increasing agent - nonaqueous. |

-continued

| Raw Material | % w/w | Function |
|---|---|---|
| Caprylyl Trimethicone | 3.000% | Skin Conditioning Agent - Occlusive |
| Euxyl PE 9010 (INCI: Phenoxyethanol & Ethylhexylglycerin) | 1.100% | Preservative |
| Tocopheryl Acetate | 0.100% | Antioxidant; Skin Conditioning Agent - Miscellaneous |
| Hyauronic Acid | 0.120% | Skin Conditioning Agent - Miscellaneous; Viscosity Increasing Agent - Aqueous |
| Sodium Tocopheryl Phosphate | 0.005% | Antioxidant; Skin Conditioning Agent - Miscellaneous |
| Hydroxysomes™ calcium phosphate particles (Laboratory Skin Care) | 1.000% | Sunscreen |
| LSC.RNB010090 | | |
| Purified Water | 48.325% | Skin Conditioning Agent - Miscellaneous; Solvent |
| Botanivera 1-200C (INCI: *Aloe barbadensis* Leaf Juice) | 0.100% | Skin Conditioning Agent - Miscellaneous |
| Xanthan Gum | 0.400% | Viscosity Increasing Agent - Aqueous; Binder; Emulsion stabilizer |
| Glycerin | 8.000% | Humectant |
| Neo Heliopan ® 303 (INCI: Octocrylene) | 6.000% | Sunscreen agent |
| Ethylhexyl Salicylate | 1.600% | Sunscreen agent |
| TiO2 (INCI: Titanium Dioxide) | 1.750% | Sunscreen agent |
| Zinc Oxide | 6.000% | Sunscreen agent |
| CCT (INCI: Caprylic/Capric Triglyceride) | 7.000% | Skin Conditioning Agent - Occlusive |
| Lipomulse 165 (INCI: Glyceryl Stearate & PEG-100 Stearate) | 2.500% | Emulsifier and emulsion stabilizer |
| Capmul 708 G (INCI: Glyceryl Caprylate) | 3.000% | Skin Conditioning agent - Emollient: Surfactant - Emulsifying agent |
| Cetyl Alcohol | 2.000% | Emulsion stabilizer; Opacifying Agent; Surfactant Emulsifying Agent |
| Stearyl Alcohol | 2.000% | Emulsion stabilizer; Opacifying Agent; Surfactant Emulsifying Agent |
| Botanisil CM-70 (INCI: Cyclotetraxsiloxane and Cyclopentasiloxane) | 5.000% | Skin Conditioning Agent - Emollient |
| Botanisil GB-20 (INCI: Cyclopentasiloxane & Dimethicone/Vinyl Dimethicone Crosspolymer) | 2.000% | Skin Conditioning Agent - Emollient & Viscosity Increasing agent - nonaqueous |
| Caprylyl Trimethicone | 3.000% | Skin Conditioning Agent - Occlusive |
| Euxyl PE 9010 (INCI: Phenoxyethanol & Ethylhexylglycerin) | 1.100% | Preservative |
| Sodium Tocopheryl Phosphate | 0.005% | Antioxidant; Skin Conditioning Agent - Miscellaneous |
| Tocopheryl Acetate | 0.100% | Antioxidant; Skin Conditioning Agent - Miscellaneous |
| Hyauronic Acid | 0.120% | Skin Conditioning Agent - Miscellaneous; Viscosity Increasing Agent - Aqueous |

II. Procedure

The following procedure was employed to prepare the above formulations:

Phase A

Add the required amount of Purified Water of Phase A into a clean, sanitized vessel. Add the required amount of Botanivera 1-200 C, Xanthan Gum and Glycerin. Start heating of Phase A to 65° C.-70° C. and mix with propeller—type mixing. Mix until dissolve and uniform. Hold temperature for phase combination.

Phase B

Prepare Phase B by combining into a suitably—sized clean and sanitized vessel, Neo Heliopan 303, Ethylhexyl Salicylate, Caprylic/Capric Triglyceride, Lipomulse 165, Capmul 708G, Cetyl Alcohol, Stearyl Alcohol, Botanisil CM-70, Botanisil GB-20, Caprylyl Trimethicone. Heat to 65° C.-70° C. with mixing until melted and uniform. Add ZnO powder and TiO2 powder. Homogenized until uniform.

Phase Combination

When both phases are at 65° C.-70° C., start adding Phase B into Phase A in the main batching vessel. Homogenize to achieve a very fine emulsion.

When the batch is free of air, commence cooling to 40° C. with propeller—type mixing. Add the required amounts of Euxyl PE 9010, Tocopheryl Acetate, Hyaluronic Acid, Sodium Tocopheryl Phosphate. Mix until uniform.

For formula 10091, in a separate vessel at R.T. add Purified Water (Part II), sodium Tocopheryl Phosphate. Mix until Sodium Tocopheryl Phosphate is dissolved. Add Hydroxysomes™ and mix for 30 minutes. Add D to C. Homogenize until uniform.

III. Testing

Formulations 10090 and 10091 were tested by Helioscreen (Marseilles, France) for SPF and UV-A blocking ability, according to the following protocols.

A. SPF

The method employed is based on the protocol initially described in B. L. Diffey and J. Robson (J.S.C.C. 40, 127-133 May/June 1989) modified and improved to evaluate the skin protection against UVB. The method consists of evaluating the Sun Protection Factor (SPF) which expresses the protection level a sun protection product brings through the full UV spectrum, using an adequate substrate on which the product has been spread, by means of a spectrophotometric method. The employed method consists in measuring the flow of UV energy through a test product (transmitted energy) and in comparing this flow to the initial flow according to the spectrophotometric method:

$T(\lambda) = I/I_0$, with $\lambda$ as the wavelength.

The wave function represented by this ratio is not sufficient to express the level of protection of the spread on the skin product as it also depends on two others wavelength functions:

Spectral irradiance of the "Standard Sun" as defined by "Commission Internationale de l'Eclairage", wave function noted $S(\lambda)$.

Erythemal action spectrum which expresses the relationship between cutaneous or subcutaneous reactions and energy of excitation light, wave function noted $E(\lambda)$.

$S(\lambda)$ and $E(\lambda)$ are known and tabulated values.

A "KONTRON 930" spectrophotometer equipped with an UV source and a double monochromator able to deliver a flow of energy between 250 and 800 nm was used. A $10^{-4}$ g precision laboratory balance to control deposited product weight was employed, where the products were deposited with a spatula. The following PMMA plates were used: HELIOPLATE® HD6 guaranteed roughness, from Helio-Screen® Labs. as substrate.

Deposition of the test sample was performed as small lined up spots all over the surface of the substrate. As deposited on the substrate, product quantity was checked by weighing. Application rate was determined in such a way that the actual quantity of product left on the substrate before equilibration was 1.2 mg/cm². The application area was greater than 16 cm², in fact about 25 cm². A PMMA plate containing UV filter was used as a reference so as to check the equipment was in good working order and to assess the relevance of carried out measures.

The in vitro SPF was expressed from the whole residual UVB and UVA spectrum having crossed the spread composition on substrate product layer. This led to a wave function $T(\lambda)$ which was multiplied by:

A first wave function $S(\lambda)$, spectral irradiance of the Standard Sun.

A second wave function $E(\lambda)$, erythemal action spectrum.

The SPF was calculated from the ratio:

$$\text{In vitro SPF} = \frac{\int_{290\,nm}^{400\,nm} E(\lambda) \cdot S(\lambda) \cdot d\lambda}{\int_{290\,nm}^{400\,nm} E(\lambda) \cdot S(\lambda) \cdot T(\lambda) \cdot d\lambda}$$

The SPF of the tested product was obtained by the calculation of the arithmetical average of the different measures: all measures corresponding to selected samples were taken into account for the calculation of the statistical dispersion.

B. UVA

The determination of the UVA protection factor or UVAPF was made using a spectrophotometric method as initially described by B. L. Diffey and J. Robson "A new substrate to measure sunscreen protection factors throughout the ultraviolet spectrum", J. Soc. Cosmet. Chem., 40, 127-133 (1989) for the SPF determination, then modified and adapted by Colipa (as reported at http://www.colipa.com/site/index.cfm?SID=15588&OBJ=26783&back=1, n°20) to evaluate the skin protection against UVA irradiation.

The employed method consisted of evaluating the protection brought by a sun protection product within the UVA range, by means of a spectrophotometric method, using an adequate substrate on which the product has been spread. The test was based on the assessment of UV transmittance through a thin film of the sun product sample, spread on a roughened substrate, before and after exposure to a controlled dose of UV radiation, from a defined UV source. Due to the possible lack of inter-laboratory reproducibility of in vitro SPF protection factor measurement, this SPF value was adjusted to the lapelled in vivo SPF through the use of a multiplying coefficient C. The sunscreen sample was exposed to an irradiation dose proportional to the initial UVA protection factor (UVAPF0), calculated from the adjusted absorbance data of the non exposed sample. The final in vitro UVA protection factor (UVAPF) is calculated from the adjusted absorbance data of the UV exposed sample.

The method used consisted of measuring the flow of UV energy through the product, expressed in transmitted energy and in comparing this flow to the initial flow according to the principle of any spectrophotometric method:

$T(\lambda) = I/I_0$ with $\lambda$ as the wavelength.

Absorbance at wavelength $\lambda$ is related to Transmittance by:

$A(\lambda) = -\log(T(\lambda))$

Absorbance values were then multiplied by different irradiances and action spectrums so as to be correlated to biological responses of in vivo methods:

For the SPF calculation:
By the source irradiance. This is the spectral irradiance of the UV source $I(\lambda)$.
And by the action spectrum related to the skin. This is the Erythema action spectrum which expresses the relationship between cutaneous or subcutaneous reactions and energy of excitation light $E(\lambda)$ (as defined by "Commission Internationale de l'Eclairage").

For the UVAPF calculation:
By the source irradiance. This is the spectral irradiance of the UV source $I(\lambda)$.
And by the action spectrum related to the skin. This is the persistent pigment darkening
(PPD) action spectrum which expresses the relationship between cutaneous or subcutaneous reactions and energy of excitation UV light $P(\lambda)$.

$I(\lambda)$, $E(\lambda)$ and $P(\lambda)$ are known and tabulated values.

The determination of the UVAPF was made through the following steps:

Step 1: In vitro measurement of absorbance $A_0(\lambda)$ through the spread on PMMA plate product prior to any UV irradiation.

Step 2: Mathematical adjustment of the initial UV spectrum using coefficient 'C' to achieve an in vitro SPF (0% UV dose) equal to the labeled (in vivo) SPF. Then initial UVA protection (UVAPF$_0$) is calculated using A$_0$($\lambda$) and C.

Step 3: A single UV dose D is calculated, proportional to UVAPF$_0$. (D=UVAPF$_0 \times 1.2$)

Step 4: UV exposure of the sample to the calculated UV dose D.

Step 5: In vitro transmission measurement of the sun product after UV exposure. Acquisition of second UV spectrum with A($\lambda$) data.

Step 6: Mathematical adjustment of the second spectrum (following UV exposure) according to the same C coefficient previously determined in step 2, then calculation of the in vitro UVA protection factor UVAPF.

A "KONTRON 930" spectrophotometer equipped with an UV source and a double monochromator able to deliver a flow of energy between 250 and 800 nm was employed; A single spot area about 1.2 cm$^2$ was evaluated. A 10$^{-4}$ g precision laboratory balance was employed to control deposited product weight. A spatula or syringe was employed deposit the product. A UV source for pre-irradiation: a CPS+SUNTEST (ATLAS) with standard and Schott WG320 filters were used. In this appliance the temperature regulation of the samples was maintained in the 20° C.-40° C. range. The following PMMA plates have been used: HELIOPLATE® HD2 guaranteed roughness, from HelioScreen® Labs. as substrate.

Deposition of the test sample was performed as small lined up spots all over the surface. As deposited on the substrate, the sample quantity was checked by weighing. Application rate was determined in such a way that the actual quantity of product left on the substrate before equilibration was 1.2 mg/cm$^2$. The application area was greater than 16 cm$^2$, in fact about 25 cm$^2$.

The spectral irradiance at the exposure plane of the artificial UV source that was used for radiation was as similar as possible to the irradiance at ground level under a standard zenith sun, as defined by COLIPA (1994) or in DIN 67501 (1999). The UV irradiance was within the following acceptance limits (measured at sample distance).

| Light source specifications | |
|---|---|
| Total UV irradiance$_{(290\ to\ 400\ nm)}$ | 50-140 W/m$^2$ |
| Irradiance ratio of UVA$_{(320\ to\ 400\ nm)}$ to UVB$_{(290\ to\ 320\ nm)}$ | 8-22 |

The reference standard sun has a total irradiance of 51.4 to 63.7 W/m$^2$ (Colipa 1994/DIN67501) and a UVA to UVB irradiance ratio of 16.9 to 17.5. The device had the ability to maintain samples below 40° C. by using air conditioning. The sample was exposed to full spectrum UV radiation but the dose is being defined by the UVA content.

For the pre-irradiation dose calculation, the Mean UVAPF$_0$ value found was 2.97 and was calculated as shown below. The single UVA applied dose was calculated to be 4 (j/cm$^2$) according to the formula:

$$D = UVAPF_0 \times D_0 \text{ in J/cm}^2$$

D$_0$ being fixed at 1.2 J/cm$^2$ UVA (in j/cm$^2$).

A PMMA plate containing UV filter was used as a reference so as to check the equipment was in good working order and to assess the relevance of carried out measures.

The in vitro SPF was calculated using the following formula:

$$SPF_{in\ vitro} = \frac{\int_{\lambda=290\ nm}^{\lambda=400\ nm} E(\lambda) * I(\lambda) * d\lambda}{\int_{\lambda=290\ nm}^{\lambda=400\ nm} E(\lambda) * I(\lambda) * 10^{-A_0(\lambda)} * d\lambda}$$

where:
E($\lambda$)=see above
I($\lambda$)=see above
A$_0$($\lambda$)=mean monochromatic absorbance of the test product layer before UV exposure
d$\lambda$=wavelength step (1 nm)

Calculation of the adjusted in vitro SPF and determination of the coefficient of adjustment C':

C is the coefficient of adjustment, iteratively determined to adjust the calculated in vitro SPF value to the labeled (in vivo) SPF value. It is recommended that C falls within a range between 0.8 and 1.2.

$$SPF_{in\ vitro, adj} = SPF \text{ labelled} = \frac{\int_{\lambda=290\ nm}^{\lambda=400\ nm} E(\lambda) * I(\lambda) * d\lambda}{\int_{\lambda=290\ nm}^{\lambda=400\ nm} E(\lambda) * I(\lambda) * 10^{-A_0 * C} * d\lambda}$$

The mean value of SPF in vivo was previously evaluated at: 11.70
Therefore, the value of the (C) coefficient was calculated at: 1.00

UVAPF$_0$ is calculated for each plate individually, according to formula:

$$UVAPF_0 = \frac{\int_{\lambda=320\ nm}^{\lambda=400\ nm} P(\lambda) * I(\lambda) * d\lambda}{\int_{\lambda=320\ nm}^{\lambda=400\ nm} P(\lambda) * I(\lambda) * 10^{-A_0(\lambda)*C} * d\lambda}$$

where: P($\lambda$)=see above
Calculation of UVAPF of plates after UV irradiation of the sample
The in vitro UVAPF was calculated using the following formula:

$$UVAPF = \frac{\int_{\lambda=320\ nm}^{\lambda=400\ nm} P(\lambda) * I(\lambda) * d\lambda}{\int_{\lambda=320\ nm}^{\lambda=400\ nm} P(\lambda) * I(\lambda) * 10^{-A_0(\lambda)*C} * d\lambda}$$

Where:
A($\lambda$) is the mean monochromatic absorbance of the test product layer after UV exposure.

Mean UVAPF0 and UVAPF Calculation:

Each plate was measured at 3 different sites to ensure that a total area of at least 2 cm$^2$ was measured. UVAPF$_0$ or UVAPF of one plate was calculated from the mean absorbance value from the 3 individual spots. When coefficient of variation of absorbance between spots exceeded 50%, then the plate was rejected and a new plate prepared. UVAPF$_0$ or UVAPF of the product was the mean of the UVAPF$_0$ or UVAPF's of three individual plates. When the coefficient of variation between the UVAPF$_0$ or UVAPF's of the individual plates exceeded 20%, then further plates have been measured until the coefficient of variation requirement was reached.

All tests corresponding to selected samples were taken into account for the calculation of the statistical dispersion.

C. CONCLUSION

|  | UVA | SPF |
|---|---|---|
| With HAX | 3-5 | 2.80 | 11.69 ± 2.40 |
| Without HAX | 3-5 | 2.50 | 9.48 ± 2.27 |

The above results demonstrate that inclusion of calcium phosphate particles in sunscreen formulations increases both the UV-A protection factor and sun protection factor of sunscreen compositions.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A sunscreen composition comprising:
uniform, rigid, spherical, nanoporous calcium phosphate particles comprising particles having a diameter of 0.1 micron or less; and
a sunscreen delivery vehicle, wherein the sunscreen delivery vehicle is an oil-in-water or water-in-oil emulsion.

2. The sunscreen composition according to claim 1, wherein the uniform, rigid, spherical, nanoporous calcium phosphate particles are ceramic.

3. The sunscreen composition according to claim 1, wherein the uniform, rigid, spherical, nanoporous calcium phosphate particles have a surface area ranging from 10 $m^2/g$ to 150 $m^2/g$.

4. The sunscreen composition according to claim 1, wherein the uniform, rigid, spherical, nanoporous calcium phosphate particles are sintered.

5. The sunscreen composition according to claim 1, wherein the uniform, rigid, spherical, nanoporous calcium phosphate particles are loaded with anti-oxidants.

6. The sunscreen composition according to claim 1, wherein the uniform, rigid, spherical, nanoporous calcium phosphate particles are loaded with an additional sunscreen.

7. The sunscreen composition according to claim 1, wherein the sunscreen delivery vehicle comprises inorganic UV shielding particles; organic UV absorbers; a polymeric water-proof component and a lipophilic component.

8. The sunscreen composition according to claim 1, wherein the uniform, spherical, nanoporous calcium phosphate particles have a porosity in the range of 30% to 85%.

9. A method comprising:
applying a sunscreen composition according to claim 1 to a keratinized skin of a subject.

10. The method according to claim 9, wherein the uniform, rigid, spherical, nanoporous calcium phosphate particles are ceramic.

11. The method according to claim 9, wherein the uniform, rigid, spherical, nanoporous calcium phosphate particles have a diameter ranging from 0.05 to 50 μm.

12. The method according to claim 9, wherein the uniform, rigid, spherical, nanoporous calcium phosphate particles have a surface area ranging from 10 $m^2/g$ to 150 $m^2/g$.

13. The method according to claim 9, wherein the uniform, rigid, spherical, nanoporous calcium phosphate particles are sintered.

14. The method according to claim 9, wherein the uniform, rigid, spherical, nanoporous calcium phosphate particles are loaded with anti-oxidants.

15. The method according to claim 9, wherein the uniform, rigid, spherical, nanoporous calcium phosphate particles are loaded with organic or inorganic UV absorbers and/or blockers.

16. The sunscreen composition according to claim 1, wherein the uniform, spherical, nanoporous calcium phosphate particles have a porosity in the range of 30% to 85%.

* * * * *